United States Patent [19]

Yamakoshi et al.

[11] Patent Number: 5,804,597

[45] Date of Patent: Sep. 8, 1998

[54] AGENT FOR THE PREVENTION OR TREATMENT OF CATARACTS

[75] Inventors: Jun Yamakoshi; Toshiaki Ariga; Hiroharu Ishikawa; Yukihiko Iwai; Tatuo Manaka; Shigehiro Kataoka; Katsumi Yuasa; Mamoru Kikuchi, all of Chiba, Japan

[73] Assignee: Kikkoman Corporation, Noda, Japan

[21] Appl. No.: 779,097

[22] Filed: Jan. 6, 1997

[30] Foreign Application Priority Data

Jun. 10, 1996 [JP] Japan .................................. 8-168664
Nov. 5, 1996 [JP] Japan .................................. 8-307514

[51] Int. Cl.$^6$ .................................................. A61K 31/35
[52] U.S. Cl. ......................................... 514/456; 514/912
[58] Field of Search ................................ 514/456, 912

[56] References Cited

U.S. PATENT DOCUMENTS

| | | | |
|---|---|---|---|
| 4,698,360 | 10/1987 | Masquelier | 514/456 |
| 4,797,421 | 1/1989 | Ariga et al. | 514/844 |
| 5,196,449 | 3/1993 | Magistretti et al. | 514/459 |

FOREIGN PATENT DOCUMENTS

| | | |
|---|---|---|
| 0 210 785 | 4/1987 | European Pat. Off. . |
| 2 699 819 | 7/1994 | France . |
| 59-59638 | 4/1984 | Japan . |
| 61-16982 | 1/1986 | Japan . |
| 3-7232 | 1/1991 | Japan . |
| 3-200781 | 9/1991 | Japan . |
| 92 06695 | 4/1992 | WIPO . |
| 93 24106 | 12/1993 | WIPO . |

OTHER PUBLICATIONS

Patent Abstracts of Japan, vol. 14, No. 470 (C–0769), 15 Oct. 1990 & JP 02 193930 A (Tsumura & Co), 31 Jul. 1990.
Tissie et al., "Oxidative Stress and Lens Opacity: An Overall Approach to Screening Anticataractous Drugs," *Ophthalmic Research*, 20:27–30 (1980).
Simonelli et al., "Oxidative Stress in Ocular Inflammation," *Chibret International Journal of Opthalmology*, 9:1–7 (1993).
Spector et al., "Hydrogen Peroxide and Human Cataract," *Experimental Eye Research*, 33:673–681 (1981).
Ariga & Asao, 1981, *Agric. Biol. Chem.* 45:2709–2712.
Delle Monache et al., 1967, *Ann. Chim.* 57:1364–1371.
R. Eastmond, 1973, *J. Inst. Brew.* 80:188–192.
Fonknechten et al., 1983, *J. Inst. Brew.* 89:424–431.
Hemingway et al., 1983, *Phytochem.* 22:275–281.
Jacques et al., 1974, *J.C.S. Perkin I* pp. 2663–2671.
S. Kumakura, 1993, *Kagakukeizai (Chem. Econ.)* 11;78–83.
A.G.H. Lea, 1978, *J. Sci. Fd Agric.* 29:471–477.
McMurrough et al., 1983, *J. Sci. Food Agric.* 34:62–72.
Nonaka et al., 1982, *Phytochem.* 21:429–432.
Nonaka et al., 1983 *Phytochem.* 22:237–241.
Derwent WPI Acc. No. 84–123450/20.
Derwent WPI Acc. No. 86–065473/10.
Derwent WPI Acc. No. 91–300280/41.
Derwent WPI Acc. No. 91–55559/08.

*Primary Examiner*—Zohreh Fay
*Attorney, Agent, or Firm*—Pennie & Edmonds LLP

[57] ABSTRACT

An agent for the prevention or treatment of cataracts comprising a proanthocyanidin oligomer is provided. The oral administration or application to the eyes of the agent of the invention produces a sufficient preventive or therapeutic effect against cataracts caused by oxidative disorders.

12 Claims, 3 Drawing Sheets

AGENT FOR THE PREVENTION OR TREATMENT OF CATARACTS

BACKGROUND OF THE INVENTION

1. Field of the Invention

The present invention relates to an agent for the prevention or treatment of cataracts. More specifically, the present invention relates to an agent for the prevention or treatment of cataracts comprising at least one proanthocyanidin oligomer.

2. Description of the Prior Art

At present, pirenoxine eye drops, reduced glutathione eye drops, salivary gland hormone tablets, thiopromine tablets, vitamins (e.g., vitamin C, vitamin E) and the like are used clinically for the prevention or treatment of cataracts (Seiji Kumakura, KAGAKUKEIZAI (Chemical Economy), 1993, November issue, pp. 78–83). However, these medicines do not produce a sufficient therapeutic effect. Although they are effective against diabetic cataract, they cannot manifest a sufficient preventive or therapeutic effect against senile cataract caused by oxidative disorders and the like.

OBJECTS AND SUMMARY OF THE INVENTION

It is an object of the invention to provide an agent for the prevention or treatment of those cataracts caused by oxidative disorders which agent can manifest a sufficient preventive or therapeutic effect against such cataracts by application to the eyes and/or by internal application.

The present inventors have made intensive and extensive researches toward the solution of the above-mentioned problems and, as a result, have found that proanthocyanidin oligomers used as antioxidants (Japanese Examined Patent Publication No. 3-7232) manifest a sufficient preventive or therapeutic effect against the cataracts caused by oxidative disorders and the like by application to the eyes and/or by internal application. The present invention has been achieved based on these findings.

The present invention relates to an agent for the prevention or treatment of the cataracts comprising at least one proanthocyanidin oligomer; the above-mentioned agent for the prevention or treatment of the cataracts wherein the proanthocyanidin oligomer is from a dimer to a 30-mer composed of flavan-3-ol units and/or units of flavan-3,4-diols represented by the following structural formula (1):

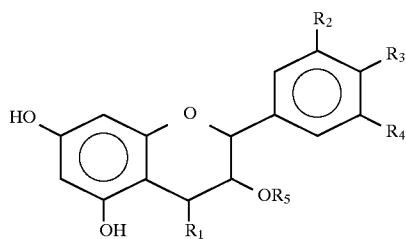

(wherein $R_1$ represents a hydrogen atom or hydroxyl group; at least one of $R_2$, $R_3$ and $R_4$ represents a hydroxyl group and they equally or independently represent a hydrogen atom, hydroxyl group or methoxyl group; and $R_5$ represents a hydrogen atom, galloyl group or glycopyranosyl group);
and the above-mentioned agent for the prevention or treatment of cataracts wherein the proanthocyanidin oligomer is an extract obtained from plant materials, preferably, e.g., grape seeds, grape peel and/or a pressed grape cake.

The horizontal axis represents the test period (days from the beginning of the application of dimer procyanidin B-3 to the eyes), and the longitudinal axis the incidence of cataract (%).

Figure 2:
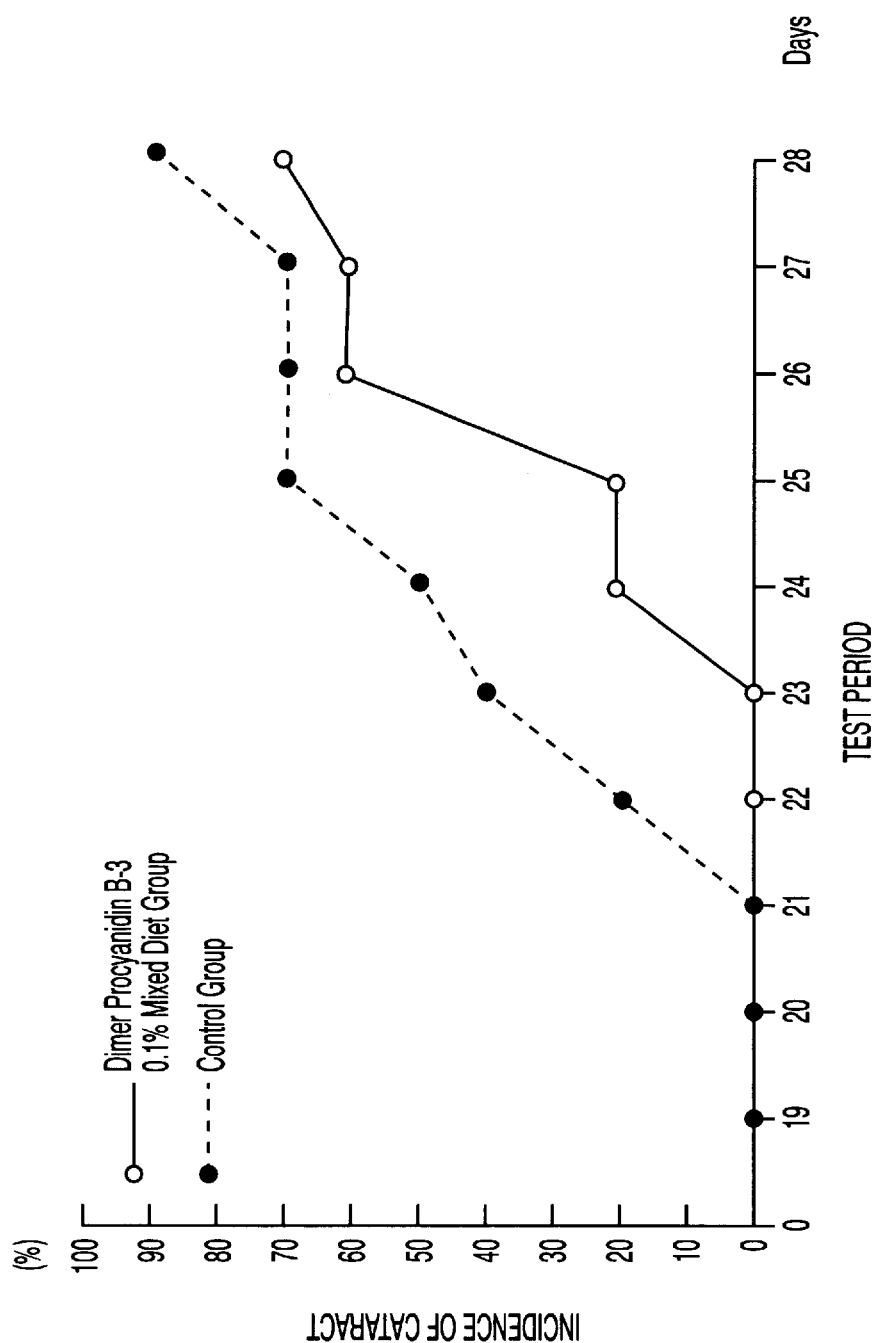

FIG. 2 shows the cataract-inhibition effect brought by the oral administration of dimer procyanidin B-3 to rats with a spontaneous cataract.

The horizontal axis represents the test period (days from the beginning of the oral administration of dimer procyanidin B-3 to the rats), and the longitudinal axis the incidence of cataract (%).

Figure 3:
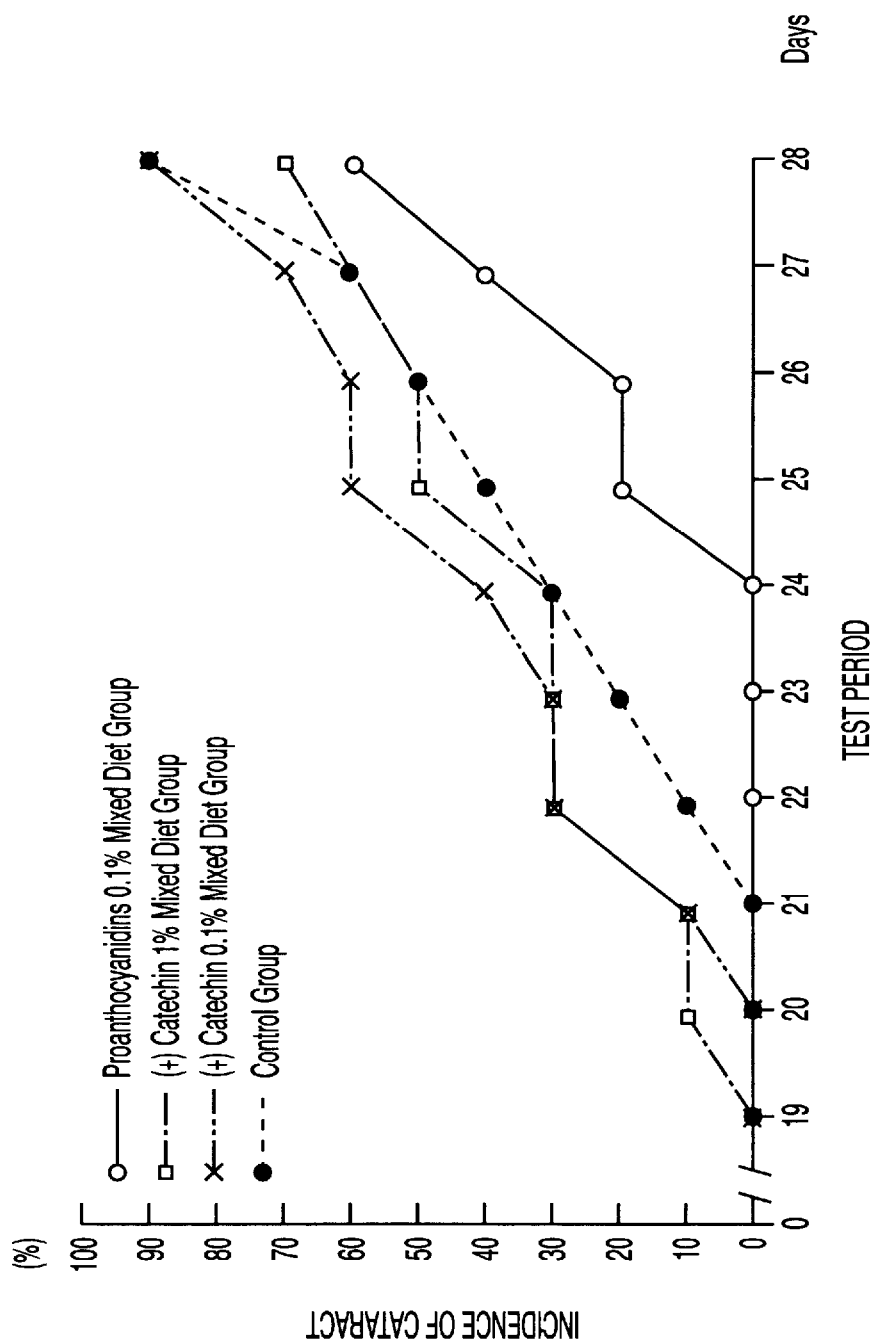

FIG. 3 shows the cataract-inhibiting effect of the proanthocyanidin oligomers obtained by extracting grape seeds on rats with a spontaneous cataract.

The horizontal axis represents the test period (days from the beginning of the oral administration of a proanthocyanidin oligomer extract to the rats), and the longitudinal axis the incidence of cataract (%).

DETAILED DESCRIPTION OF THE INVENTION

Hereinbelow, the present invention will be described in detail.

The present invention is characterized by an agent for the prevention or treatment of cataracts comprising at least one proanthocyanidin oligomer. The proanthocyanidin oligomers of the invention include, in addition to the above oligomer themselves and salts thereof, materials containing at least one oligomer, e.g., a plant material containing at least one of the oligomers or crushed material thereof, and an extract of such a plant material or a purified material obtained from such an extract. Further, various mixtures of proanthocyanidin oligomers or mixtures of a proanthocyanidin oligomer(s) and a material(s) containing a proanthocyanidin oligomer(s) are also included. These materials are included in the present invention regardless of the method of preparation.

As to a plant, any plant may be used as long as it can achieve the object of the invention. Specific examples include grape, adzuki bean (Vigna angularis), horse chestnut, pine, oak, knotgrass, myrica, barley, ouratea, apple, persimmon, cranberry, berry, cacao, black soybean, Japanese cypress, and Japanese cedar.

As to a plant material, any portion of a plant may be used as long as the portion can achieve the object of the present invention. For example, flowers, nuts, seeds, fruits, flesh or peel thereof, roots, woods, bark, leaves and the like may be used. They may be either dry or raw. Further, fruit juices or apple cider, fruit wines such as one from grapes, beers, a cake produced as a by-product during a process of producing wine or beer, a material obtained by processing a plant material and the like may also be used.

As a plant material to be used in the present invention, grape seeds, grape peel or a pressed grape cake is particularly preferable from the viewpoint of safety. As a pressed cake, a cake produced during a process of producing grape juice or wine may be given.

Specific examples of the proanthocyanidin oligomers include a group of compounds which are obtainable by binding several units of flavan-3-ol, flavan-3,4-diols and/or flavan-4-ol, or a derivative thereof as constitutional units through condensation or polymerization. (Various polymers or condensates produced by chemical synthesis, condensed tannin present in various plant materials, or various anthocyanidin compounds of cyanidin type, delphinidin type, pelargonidin type or the like obtained by the hydrolysis of plant materials may be enumerated.)

Of the group of compounds described above, preferable are various anthocyanidin compounds of procyanidin type, prodelphinidin type, propelargonidin type or the like which are dimers, trimers, tetramers or even polymers greater than 30-mers wherein a number of the constitutional units described above are bound together; stereoisomers thereof; or various derivatives thereof. As to the production method, chemical or enzymatic synthesis, extraction from a plant material or a microorganism and the like may be enumerated.

Of the compounds described above, preferable proanthocyanidin oligomers in terms of solubility of the compound per se, bioabsorption, localized action or activity as a medicine are dimers to 30-mers composed of flavan-3-ol units and/or units of flavan-3,4-diols represented by the above-mentioned general formula (1) as constitutional units (see Japanese Unexamined Patent Publication No. 61-16982). Of those oligomers, particularly preferable are dimers to 10-mers. Thus, the agent of the invention for the prevention or treatment of cataracts comprises at least one proanthocyanidin oligomer selected from the group of compounds described above, preferably from the dimers to 30-mers described above.

Hereinbelow, the proanthocyanidin oligomer of the invention will be described more specifically.

A proanthocyanidin oligomer (a dimer to a 30-mer) composed of flavan-3-ol units and/or units of flavan-3,4-diols represented by the above-mentioned general formula as constitutional units can be obtained by a known chemical or enzymatic synthesis or by extraction from various plant materials.

As to the extraction method, for example, various plant materials or crushed materials obtained therefrom are extracted using a solvent, and the resultant extract is fractionally purified by liquid chromatography and the like. Alternatively, a secondary processed product such as a fruit wine or beer produced from a plant material is treated with a selective adsorbent for a proanthocyanidin oligomer to thereby concentrate the proanthocyanidin oligomer fraction, and then the concentrated fraction is fractionally purified by the countercurrent distribution method, liquid chromatography and the like.

In the present invention, it is particularly preferable to treat grape seeds, grape peel or a pressed grape cake with hot water, ethanol hydrate or acetone hydrate to extract the proanthocyanidin oligomer of the invention and to thereby obtain the oligomer of interest as an extract or a mixture.

Various proanthocyanidin oligomers and methods for producing the same are illustrated as follows.

(1) Method for Producing the Proanthocyanidin Oligomer of the Invention as An Extract from Grape Seeds, Grape Peel or a Pressed Grape Cake A known method (Japanese Unexamined Patent Publication No. 3-200781) may be used. For example, grape seeds, grape peel or a pressed grape cake is subjected to hot water extraction at 70° C. or above, preferably at 70°–120° C., most preferably at 80°–100° C. At this time, usually, the amount of water used is 1–20 times (v/w), preferably 3–10 times (v/w) based on the amount of the seeds, peel or cake. The time of extraction is appropriately selected to give a maximum extract. Usually, this time is 10 minutes to 4 hours, preferably 15 minutes to about 2 hours.

In the present invention, an extract obtained at this stage or a dried or purified material (including a partially purified material) obtained therefrom may be used as the extract from grape seeds, grape peel or a pressed grape cake of the invention, but preferably these materials are treated as described below to obtain the extract of the invention.

Briefly, prior to the hot water extraction, the raw material is contacted with 1–20 times (v/w), preferably 3–10 times (v/w) of water at less than 70° C., preferably at 20°–70° C. for 5 minutes to 4. hours, preferably for 10 minutes to 2 hours to thereby remove impurities such as saccharides contained in the raw material. Thereafter, the proanthocyanidin oligomer of the invention is extracted. According to these procedures, the oligomer of interest is obtained at a high purity. In this case, the proanthocyanidin oligomer of the invention obtained is a mixture of various proanthocyanidin oligomers.

This extract, which itself is the proanthocyanidin oligomer of the invention, may be dried further by various conventional procedures. Various purification procedures may also be conducted to obtain purified products of various stages (including partially purified products).

In the present invention, all of those extracts, dried products and purified products described above are defined as the extract of the present invention.

(2) Dimer Procyanidin B-2 ($C_4$–$C_8$ Bound), $C_4$–$C_8$ Bound Dimer Procyanidin ($C_4$–$C_8$ Bound)

These compounds may be obtained by fractionally purifying a 70% aqueous acetone extract of adzuki bean (*Vigna angularis* Ohwiet Ohashi) by liquid chromatography using a Polyamide C-200 column and a Sephadex LH-20 column according to the method described by a part of the present inventors (Ariga et al.) in Agric. Biol. Chem., Vol. 45, pages 2709–2712 (1981).

(3) Dimer Proanthocyanidin A-2

This compound may be obtained from nutshells of horse chestnut (*Aesculus hippocastanum*) according to the method of D. Jacques et al. described in J. C. S. Perkin I, pages 2663–2671 (1974).

(4) $C_4$–$C_8$ Bound Dimer Procyanidin ($C_4$–$C_8$ Bound)

This compound may be obtained from the bark of Lobolly pine according to the method of R. W. Hemingway described in Phytochemistry, Vol. 22, pages 275–281 (1983).

(5) $C_6$–$C_8$ Bound Dimer Prodelphinidin ($C_6$–$C_8$ Bound)

This compound may be obtained from the bark of oak according to the method of Byung-Zun Ahn et al. described in Arch. Parmaz., pages 666–673 (1970).

(6) Procyanidin B-1-Gallic Acid Ester ($C_4$–$C_8$ Bound), Procyanidin B-1 Digallic Acid Ester ($C_4$–$C_8$ Bound)

These esters may be obtained from roots of knotgrass (*Polygonum multiflorum*) according to the method of Nonaka et al. described in Phytochemistry, Vol. 21, pages 429–432 (1982).

(7) Dimer Prodelphinidin B-2 Digallic Acid Ester ($C_4$–$C_8$ Bound)

This ester may be obtained from the bark of myrica (Myricarubra) according to the method of Nonaka et al. described in Phytochemistry, Vol. 22, pages 237–241 (1983).

(8) $C_4$–$C_8$ Bound Dimer Propelargonidin ($C_4$–$C_8$ Bound), $C_4$–$C_8$ Bound Trimer Prodelphinidin ($C_4$–$C_8$ Bound)

These compounds may be obtained from barley and malt according to the method of I. Mcmurrough et al. described in J. Sci. Food Agric., Vol. 34, pages 62–72 (1983).

(9) Dimer Procyanidin B-4 Rhamnoside

This compound may be obtained from the coats of *Kandelia candel* according to the method described in Japanese Unexamined Patent Publication No. 59-59638.

(10) $C_4$–$C_8$ Bound Dimer Propelargonidin ($C_4$–$C_8$ Bound)

This compound may be obtained from the coats of roots of ouratea according to the method of F. D. Monache et al. described in Ann. Chim. (Rome), Vol. 57, pages 1364–1371 (1967).

(11) $C_4$–$C_8$ Bound Tetramer Procyanidin ($C_4$–$C_8$ Bound)

This compound may be obtained by fractionally purifying a proanthocyanidin concentrate obtained by treating apple cider with Sephadex LH-20 by the countercurrent distribution method using acetate and water and liquid chromatography using a Sephadex LH-20 column according to the method of A. G. H. Lea described J. Sci. Food Agric., Vol. 29, pages 471–477 (1978).

As to the method of synthesis, the following example may be given.

(12) Dimer Procyanidin B-3 ($C_4$–$C_8$ Bound), Dimer Procyanidin B-4 ($C_4$–$C_8$ Bound)

These compounds may be obtained from dihydroquercetin and catechin or epicatechin by synthesis according to the method of G. Fonknechten et al. described in J. Inst. Brew., Vol. 89, pages 424–431 (1983). Alternatively, these compound may be obtained by the method of synthesis of R. Eastmond described in J. Inst. Brew., Vol. 80, page 188 (1974).

In addition to the compounds described above, also obtainable by chemical synthesis are a procyanidin dimer (A-1), a prodelphinidin dimer, a procyanidin trimer, a procyanidin tetramer and the like.

By the methods described above, the proanthocyanidin oligomer of the invention is obtained in the state of liquid or semisolid. By treating (e.g., freeze-drying) the thus obtained oligomer further, the proanthocyanidin oligomer of the invention may be obtained in a powder form.

Pharmacologically acceptable salts of the above-mentioned proanthocyanidin oligomer may also be used in the agent of the invention for the prevention or treatment of cataracts. Specific examples of such salts include alkali metal salts (e.g., sodium salts, potassium salts), alkaline earth metal salts (e.g., calcium salts), ammonium salts, ethanol amine salts, triethylamine salts, dicyclohexylamine salts, and the like.

Action

The proanthocyanidin oligomer of the invention exhibits an extremely strong antioxidation activity. Therefore, it is presumed that the oligomer of the invention exhibits an anticataract effect by inhibiting the oxidation reaction in the lens during the process of cataractogenesis.

Method of Administration

The agent of the invention for the prevention or treatment of cataracts may be appropriately administered orally or parenterally for the prevention or treatment of those cataracts associated with oxidative disorders, such as senile cataract. In other words, the agent of the invention exhibits a remarkable therapeutic effect not only by oral, intravenous or intraperitoneal administration but by application to the eyes.

Formulations

The agent of the invention may be formulated into any of solid formulations such as tablets, grains, powder and capsules, and liquid formulations such as eye drops and injection solutions by known methods. These formulations may appropriately include conventionally-used excipients such as a binder, disintegrant, thickener, dispersant, reabsorption promoting agent, flavor, buffer, surfactant, resolvent, preservative, emulsifier, isotonicity inducing agent, stabilizer and pH modifier.

Dose

The dose of the proanthocyanidin oligomer of the invention used for the purpose of the invention varies depending on the kind of the oligomer, the formulation, and the age, weight and conditions of a patient. For example, in the case of an injection solution, about 0.01–1000 mg, preferably about 0.1–100 mg of the proanthocyanidin oligomer is administered once a day per adult, and in the case of an internal medicine, about 0.1–4000 mg, preferably about 1–3000 mg of the proanthocyanidin oligomer is administered several times a day per adult. In the case of eye drops, one or two drops of the formulation with the proanthocyanidin oligomer concentration of 0.01–10% (w/w), preferably 0.5–2% (w/w) are applied to the eyes one to five times, preferably two to five times a day.

In the present invention, the agent of the invention for the prevention or treatment of cataracts and/or components producing different pharmaceutical effects may be combined appropriately.

In the case of the above-mentioned oral administration, the proanthocyanidin oligomer of the invention may also be used as health food. Alternatively, the proanthocyanidin oligomer of the invention may be added to food and drink, which may then be taken.

In the former case, the amount of the proanthocyanidin oligomer to be added to food and drink is not particularly limited. In the latter case, the amount is 0.01–5% (w/w), preferably 0.5–2% (w/w).

PREFERRED EMBODIMENTS OF THE INVENTION

The present invention will be described more specifically below with reference to the following Test Examples and Examples, which should not be construed as limiting the scope of the invention.

Test Example 1

Synthesis of Dimer Procyanidin B-3 ($C_4$–$C_8$ Bound)

Based on the method of R. Eastmond (J. Inst. Brew., 80: 188, 1974), a synthetic reaction was carried out using 50 g of (±)-dihydroquercetin, 50 g of (+)-catechin and sodium borohydride as starting materials. After the completion of the reaction, the pH of the reaction solution was adjusted to 5.0 with acetic acid, and then an extraction operation was conducted using ethyl acetate. The resultant extract was subjected to vacuum distillation, and the concentrate obtained was loaded to a column packed with Sephadex LH20 ($\phi$8×65 cm). The concentrate was fractionated by column chromatography using ethanol as a developing solvent. By collecting 9–131 fractions, the fraction of dimer procyanidin B-3 was obtained.

This fraction was purified by reversed phase silica gel HPLC [column: $\mu$Bondapack $C_{18}$ (50×300 mm); developing solvent: 7.5% methanol; detection: $OD_{280nm}$] based on the method of Ariga et al. (Agric. Biol. Chem., 52: 2717–2722, 1988). By freeze-drying the eluted fraction of interest, 5.11 g of dimer procyanidin B-3 was obtained.

Test Example 2

Production of a Proanthocyanidin Oligomer Extract from Grape Seeds

To 1 kg of seeds of white grapes, 5 liters of water was added, and agitated and washed at 55° C. for 2 hours. Then, the seeds were completely washed with another 5 liters of water. The washed seeds were extracted with 5 liters of distilled water at 90° C. for 3 hours. The crude extract was filtered by a conventional method. The resultant clear solution was concentrated to 10 Brix degree and then left standing overnight. The precipitate generated was removed by centrifugation and the resultant clear solution was concentrated and then freeze-dried, to thereby obtain 27.2 g of proanthocyanidin oligomer content was conducted as follows. First, total flavanols were measured according to the method of R. B. Broadhurst et al. described in J. Sci. Fd. Agric., Vol. 29, pages 788–798 (1978). Then, the content of monomer catechins was measured according to the method of S. Kitao et al. (Biosci. Biotech Biochem., 57: 2010–2015, 1993). The proanthocyanidin oligomer content was calculated by deducting the value obtained in the latter measurement from the value obtained in the former measurement.

Test Example 3

Anticataract Effect upon ICR/f Rats with Spontaneous Cataract brought by the Application to the Eyes of the Dimer Procyanidin B-3 Sample obtained in Test Example 1

(Testing Method)

This test was conducted using 8-week old, male ICR/f rats (7–8 rats/group; average body weight: 190 g). Dimer procyanidin B-3 was applied to the eyes of rats three times a day (in the morning, noon and evening) for 4 weeks. The dimer procyanidin B-3 eye drops were prepared as a liposome containing the dimer procyanidin B-3 by dissolving dimer procyanidin B-3 in saline at a rate of 1% and then adding thereto dipalmitoylphosphatidylcholine (DPPC; Nippon oils a Fats Co., Ltd.) at a rate of 0.5%. As a control, saline alone was applied to the eyes of rats in a similar manner. During the test period, at intervals of 1 week, mydriasis was conducted with mydrin P (Santen Pharmaceutical Co., Ltd.) and then slit images of the lens and an entire image of the anterior ocular segment were photographed with Nikon Zoom Slit Lamp Microscope FS-3 (Nikon). The rats tested were classified into 6 stages of from 0 to 5 according to the method of Nishida et al. [ATARASHII GANKA (New Ophthalmology), Vol. 2, No. 9, pp. 1307–1312]. The ICR/f rats used in the test were already at stage 3 (cloudiness in the lens is not recognized by the eyes, but slight turbidity is observed in the posterior subcapsule in a slit image) at the beginning of the test. During the test period, the time point at which turbidity in the lens progressed to stage 4 (cloudiness in the lens is recognized by the eyes) was considered as the onset of a cataract. The incidence of cataract (%) was calculated by the following formula:

Number of eyes with a cataract/Total Number of Eyes×100

(Test Results)

Figure 1:
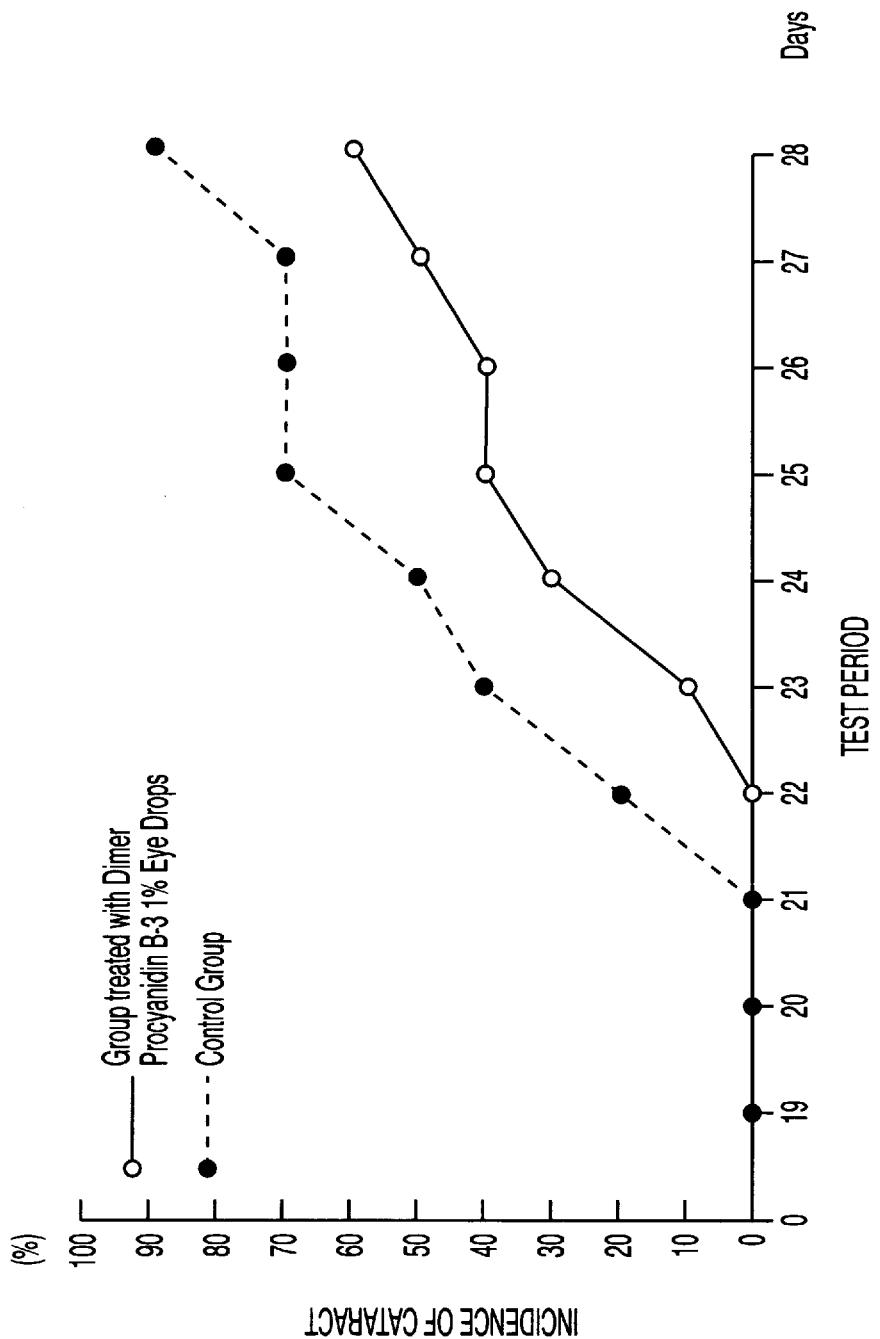
FIG. 1 shows the cataract-inhibition effect brought by the application of dimer procyanidin B-3 to the eyes of rats with a spontaneous cataract.

The test results are shown in FIG. 1. In the control group, remarkable cloudiness in the lens began to be observed as time passed, and the incidence of cataract reached 90% four weeks from the beginning of the test. On the other hand, the group treated with the dimer procyanidin B-3 eye drops exhibited a delay of one day in the onset of a cataract (the day when rats progressed from stage 3 to stage 4) compared to the control group. The incidence of cataract in this group was 60% four weeks from the beginning of the test.

Test Example 4

Anticataract Effect upon ICR/f Rats brought by the Oral Administration of the Dimer Procyanidin B-3 Sample obtained in Test Example 1

(Testing Method)

This test was conducted using 8-week old, male ICR/f rats (7–8 rats/group; average body weight: 190 g). Dimer procyanidin B-3 was added to MF powder feed (Oriental Yeast Co., Ltd.) at a rate of 0.1%, and the treatment group was allowed to take this mixed diet freely for 4 weeks. On the other hand, the control group was allowed to take MF powder feed alone freely for 4 weeks. During the test period of 4 weeks, photographs were taken at intervals of 1 week in the same manner as described in Test Example 3, and the incidence of cataract was calculated.

(Test Results)

The test results are shown in FIG. 2. In the control group, remarkable cloudiness in the lens began to be observed as time passed, and the incidence of cataract reached 90% four weeks from the beginning of the test. On the other hand, the treatment group fed with the mixed diet containing 0.1% of dimer procyanidin B-3 exhibited a delay of two days in the onset of a cataract compared to the control group, and the incidence of cataract in this group was 70% four weeks from the beginning of the test. The amount of dimer procyanidin B-3 intake in the rats of the treatment group was 72 mg/kg/day in the average.

Test Example 5

Anticataract Effect of the Proanthocyanidin Oligomer Extract described above upon ICR/f Rats (Testing Method)

This test was conducted using 8-week old, male ICR/f rats (7–8 rats/group; average body weight: 190 g). The proanthocyanidin oligomer extract was added to MF powder feed (Oriental Yeast Co., Ltd.) at a rate of 0.1%. One group was allowed to take this mixed diet freely for 4 weeks (proanthocyanidin oligomer mixed diet group). For the purpose of comparison, (+) catechin was mixed in MF powder feed at rates of 1% and 0.1%, respectively, and two groups were allowed to take these mixed diets, respectively, freely for 4 weeks [(+) catechin 1% mixed diet group and (+) catechin 0.1% mixed diet group]. As a control, one group was allowed to take MF powder feed alone freely for 4 weeks. During the test period of 4 weeks, photographs were taken at intervals of 1 week in the same manner as described in Test Example 3, and the incidence of cataract was calculated.

(Test Results)

The test results are shown in FIG. 3. In the control group, remarkable cloudiness in the lens began to be observed as time passed, and the incidence of cataract reached 90% four weeks from the beginning of the test. On the other hand, the proanthocyanidin oligomer mixed diet group exhibited a delay of three days in the onset of a cataract (the day when rats progressed from stage 3 to stage 4) compared to the control group, and the incidence of cataract in this group was 60% four weeks from the beginning of the test. In the (+) catechin 1% mixed diet group and the (+) catechin 0.1% mixed diet group, anticataract effect was not observed. The amount of proanthocyanidin oligomer intake in the proanthocyanidin oligomer mixed diet group was 72.8 mg/kg/day in the average. The amount of (+) catechin in take in the (+) catechin 1% mixed diet group was 732.5 mg/kg/day in the average, and the amount of (+) catechin in take in the (+) catechin 0.1% mixed diet group was 71.6 mg/kg/day in the average.

Test Example 6

Single Dose Toxicity Test (Testing Method)

This test was conducted using 5-week old, male and female Crj: ICR mice (average body weight in male mice: 27 g; average body weight in female mice: 22 g) (5 mice/group). A dimer procyanidin B-3 sample and a proanthocyanidin oligomer produced in substantially the same manner as described in Test Examples 1 and 2, respectively, were tested. These compounds were orally administered to different male and female mice in an amount of 2 g/kg as a compelled, single dose, and then the mice were observed for 14 days. As a control group, male and female mice were administered distilled water alone in a similar manner. After the completion of the test, all of the mice were subjected to pathological anatomy to thereby confirm the presence or absence of abnormality in each organ.

(Test Results)

No mice died as a result of the administration of the above-mentioned compound. Male and female mice exhibited no clinical symptoms and showed a steady increase in their body weights during the test period. No abnormalities were found in the pathological anatomy of all of the mice after the completion of the test.

EXAMPLES

Formulation Example 1 (Eye Drops)

| | |
|---|---|
| Dimer procyanidin B-3 (obtained in Test Example 1) | 1.0 g |
| Boric acid | 0.7 g |
| Sodium chloride | 0.6 g |
| Methyl P-oxybenzoate | 0.02 g |
| Chlorobutanol | 0.3 g |

The above components were dissolved in sterile purified water to give a total volume of 100 ml (pH was adjusted to 6.0 with sodium hydroxide).

Formulation Example 2 (Internal Medicine)

| | |
|---|---|
| Proanthocyanidin oligomer extract (obtained in Test Example 2) | 100 mg |
| Lactose | 80 mg |
| Starch | 17 mg |
| Magnesium stearate | 3 mg |

The above components were made into one tablet.

Formulation Example 3 (Internal Medicine)

| | |
|---|---|
| Dimer procyanidin B-3 (obtained in Test Example 1) | 100 mg |
| Lactose | 80 mg |
| Starch | 17 mg |
| Magnesium stearate | 3 mg |

The above components were made into one tablet.

Formulation Example 4 (Injection Solution)

| | |
|---|---|
| Dimer procyanidin B-3 (obtained in Test Example 1) | 1.5 g |
| Sodium chloride | 0.6 g |
| Distilled water for injection | 100 ml |

The above components were mixed and sterile filtration was conducted using 0.45 μm Mini Capsule Filter (Gelman Science). The filtrate was packed in a glass ampule by 2 ml and the ampule was sealed up by melting, to thereby obtain an injection solution.

EFFECT OF THE INVENTION

As seen from the Test Examples described above, the agent of the invention for the prevention or treatment of cataracts is weak in toxicity and can be advantageously used for the prevention or treatment of senile cataract.

What is claimed is:

1. A method for the treatment or prevention of cataracts in a mammal, which method comprises administering to the mammal a therapeutically effective amount of a composition comprising at least one proanthocyanidin oligomer or a salt thereof, wherein the proanthocyanidin oligomer is from a dimer to a 30-mer comprising monomers each of which has the formula

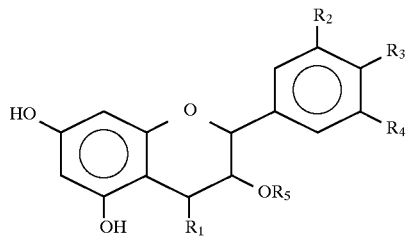

wherein $R_1$ is hydrogen or a hydroxyl group; $R_2$, $R_3$ and $R_4$ are each independently hydrogen, a hydroxyl group or a methoxy group, provided that at least one of $R_2$, $R_3$ and $R_4$ is a hydroxyl group; and $R_5$ is hydrogen, a galloyl group or a glycopyranosyl group.

2. The method according to claim 1, wherein the mammal is a human.

3. The method according to claim 1, wherein the proanthocyanidin oligomer is from a dimer to a 10-mer.

4. The method according to claim 1, wherein the composition comprises a proanthocyanidin oligomer-containing extract obtained from a plant material.

5. The method according to claim 4, wherein the plant material is grape seeds, grape peel or pressed grape cake.

6. The method according to claim 1, wherein the composition is administered orally.

7. The method according to claim 1, wherein the composition is administered parenterally.

8. The method according to claim 1, wherein the composition is formulated as a tablet, a grain, a powder, a capsule, an eye drop or an injection solution.

9. The method according to claim 1, wherein the composition further comprises a binder, disintegrant, thickener, dispersant, reabsorption promoting agent, flavorant, buffer, surfactant, resolvent, preservative, emulsifier, isotonicity inducing agent, stabilier or pH modifier.

10. The method according to claim 8, wherein the composition is formulated as an injection solution, and the amount administered is a dosage of about 0.01 to 1000 mg, which dosage is administered once daily.

11. The method according to claim 8, wherein the composition is formulated as an eye drop with a concentration of the proanthocyanidin oligomer of 0.01 to 10% (w/w), and the amount administered is a dosage of one to two drops, which dosage is administered to the eye of the animal one to five times a day.

12. The method according to claim 6, wherein the composition is formulated as a food or an additive to a food or drink.

* * * * *

UNITED STATES PATENT AND TRADEMARK OFFICE
CERTIFICATE OF CORRECTION

PATENT NO. : 5,804,597

DATED : September 8, 1998

INVENTOR(S) : YAMAKOSHI et al.

It is certified that error appears in the above-identified patent and that said Letters Patent is hereby corrected as shown below:

TITLE PAGE, Col. 1, "OTHER PUBLICATIONS"

line 5, change "(1980)." to --(1988).--;

line 7, change "Opthalmology," to --Ophthalmology,--.

Signed and Sealed this

Fifteenth Day of December, 1998

Attest:

BRUCE LEHMAN

Attesting Officer     Commissioner of Patents and Trademarks